United States Patent [19]

Odenwälder et al.

[11] 4,360,581

[45] Nov. 23, 1982

[54] COLOR PHOTOGRAPHIC RECORDING MATERIAL CONTAINING NON-DIFFUSING ELECTRON DONOR COMPOUNDS

[75] Inventors: Heinrich Odenwälder, Leverkusen; Hans Vetter, Cologne, both of Fed. Rep. of Germany; Wilhelmus Janssens, Aarschot; Jan Jaeken, Hove, both of Belgium

[73] Assignee: Agfa-Gevaert Aktiengesellschaft, Leverkusen, Fed. Rep. of Germany

[21] Appl. No.: 208,187

[22] Filed: Nov. 19, 1980

[30] Foreign Application Priority Data

Nov. 24, 1979 [DE] Fed. Rep. of Germany ....... 2947425

[51] Int. Cl.³ ............................ G03C 5/54; G03C 1/40
[52] U.S. Cl. ..................................... 430/218; 430/222; 430/223; 430/559
[58] Field of Search ............... 430/218, 222, 223, 559, 430/440, 442, 483, 484

[56] References Cited

U.S. PATENT DOCUMENTS

| | | | |
|---|---|---|---|
| 4,076,529 | 2/1978 | Fleckenstein et al. | 430/223 |
| 4,139,379 | 2/1979 | Chasman et al. | 430/223 |
| 4,139,389 | 2/1979 | Hinshaw et al. | 430/223 |
| 4,198,235 | 4/1980 | Vetter et al. | 430/222 |
| 4,205,987 | 6/1980 | Erikson et al. | 430/216 |
| 4,258,120 | 3/1981 | Gerbal et al. | 430/559 |
| 4,263,393 | 4/1981 | Chen | 430/218 |
| 4,278,750 | 7/1981 | Chen | 430/218 |

OTHER PUBLICATIONS

Research Disclosure, pp. 94–97, Item 17842, Feb. 1979.

*Primary Examiner*—J. Travis Brown
*Attorney, Agent, or Firm*—Connolly and Hutz

[57] ABSTRACT

Electron donor compounds of the formula I are effective to reduce non-diffusing reducible color providing compounds which when reduced release under the photographic development conditions a diffusible dye.

$$R^1(-L^1=L^2)_n-NH-SO_2-X \qquad (I)$$

in which
L¹, L² represent methine groups which may be part of a carbocyclic or heterocyclic ring
R¹ represents —OR², —SR² or —NHR³
R² represents H or a hydrolysable group
R³ represents H, alkyl, aryl, acyl including a group that together with L¹ completes a ring
n=1 or 2
X represents a non-colored organic group.

3 Claims, No Drawings

COLOR PHOTOGRAPHIC RECORDING MATERIAL CONTAINING NON-DIFFUSING ELECTRON DONOR COMPOUNDS

This invention relates to a color photographic recording material containing non-diffusible, reducible color providing compounds which, when in the reduced state, release diffusible dyes under the conditions of alkaline development, said color photographic material also containing reducing sulfonamide compounds to serve as reducing agents or so-called electron donor compounds, hereinafter referred to as ED compounds, for the color providing compounds.

Color providing compounds having an electron accepting nucleophilic precursor group have been described in German Offenlegungsshcrift No. 2,809,716. In the reduced state, these compounds are subjected to an intramolecular nucleophilic displacement reaction in which they release a diffusible dye. The reduction is brought about by so-called electron donor compounds (ED compounds) which are contained in the layers together with the color providing compounds and which are oxidized imagewise by development and thereby used up. The ED compounds remaining behind in imagewise distribution react with the color-providing compounds to bring about the imagewise release of diffusible dyes. The ED compounds described in the said Offenlegungsschrift include, for example derivatives of benzisoxazolone, hydroquinone, p-aminophenol and ascorbic acid. In order to obtain high quality images by the process described in German Offenlegungsschrift No. 2,809,716, the ED compounds are required not only to reduce the color providing compounds but also to allow themselves to be oxidized by exposed silver halide or by silver halide developer oxidation products. In addition, the velocities of the oxidation reaction and of the reducing reaction must be adjusted optimally to each other so that the ED compounds will already be oxidized to a considerable extent during development before it reduces the color providing compound. The known ED compounds do not satisfy these requirements in every respect, as may be seen, for example, from an insufficient color density and/or an unacceptable degree of color fog in the color transfer images produced.

It is an object of the present invention to provide new ED compounds for the dye diffusion transfer process which satisfy the requirements with regard to their capacity to reduce and to be oxidized and which are superior to the known ED compounds in the quality of the color images produced. This object is fulfilled by the color photographic recording material described below.

The invention relates to a color photographic recording material having at least one silver halide emulsion layer and, associated with this layer, a combination of a non-diffusing, reducible color providing compound which, in its reduced state, is capable of releasing a diffusible dye under alkaline conditions of development and a non-diffusing electron donor compound (ED compound) which is capable of reducing the non-diffusing, reducible color providing compound under the alkaline development conditions, characterized in that the material contains, as ED compound, a compound corresponding to the following general formula:

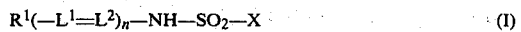

$$R^1(-L^1=L^2)_n-NH-SO_2-X \qquad (I)$$

in which $L^1$, $L^2$ each represent a methine group which may be substituted and which may be part of an at least partially unsaturated, preferably aromatic, carbocyclic or heterocyclic ring system;

$R^1$ represents $-OR^2$, $-SR^2$ or $-NHR^3$;

$R^2$ represents hydrogen or a group which is capable of being hydrolysed under the conditions of photographic development, e.g. an acyl group;

$R^3$ represents hydrogen, alkyl, aryl, acyl or a group which, together with the nitrogen atom present in $R^1$ and with $L^1$, optionally with the inclusion of $L^2$, completes a ring system having at least one 5-, 6- or 7-membered heterocyclic ring;

n represents 1 or 2, and

X represents any colorless organic group.

The group X is not subject to any limitations apart from the fact that it should not be colored or at least should not cause any coloration. The main reason for this lack of limitation is that the effectiveness of the ED compounds in their use according to the invention is largely unaffected by the nature of the group X. This makes possible a wide variation in the choice of X according to requirement. X may be, for example, a relatively small molecular group which, after it has been released from the ED compound (as $H_2N-SO_2-X$), is relatively mobile in the photographic layers or in the alkaline developer medium, or a group which, due to its size, is immobile in the layers. The groups generally chosen for X are of the kind which are photographically inert so that the presence of these groups in the photographic layers will in no way impair the photographic properties. On the other hand, the characteristic reactivity of the compounds according to the invention may be utilized by equipping the ED compounds with groups X which have the property of producing certain effects in the photographic layers when released in the form of $H_2N-SO_2-X$. The choice of a suitable group X therefore depends on its required function. The groups used for X may be, for example, any aliphatic or aromatic or even heterocyclic groups, and they may in turn be substituted with a wide variety of substituents. Examples of groups X include methyl, n-hexadecyl, dimethylamino, phenyl, naphthyl, p-dodecylphenyl, p-tolyl, 3,4-dichlorophenyl, 4-dodecyloxyphenyl, 3-carboxyphenyl, 3-aminophenyl and 4-N-n-dodecylcarbamoylaminophenyl.

When n has the value 2, the groups $R^1$ and $-H-N-SO_2-X$ are preferably in the 1,4-positions of a benzene ring which may in addition contain condensed carbocyclic or heterocyclic rings, in which case the groups $L^1$ and $L^2$ are present each twice and in alternating sequence. The two methine groups represented by the same symbol ($L^1$, $L^2$) need not necessarily be identical as regards their substitution. But n preferably has the value 1 so that $R^1$ and the group $-NH-SO_2-X$ are attached to different carbon atoms of a vinylene group. The latter may be part of an at least partially unsaturated, preferably aromatic carbocyclic or heterocyclic ring which preferably has 5, 6 or 7 ring members in the form of carbon or hetero atoms and which may also contain other rings in a condensed form. Such rings may also include the group $R^1$ in their formation.

Examples of suitable ED compounds include compounds corresponding to the following formula

in which $R^1$ represents $-OR^2$, $-SR^2$ or $-NHR^3$, $R^2$ represents hydrogen or a group which is capable of being hydrolysed under the conditions of photographic development, e.g. an acyl group, $R^3$ represents hydrogen, alkyl, aryl, acyl or a group which, together with $R^4$ or with $R^5$ or with $R^4$ and $R^5$, completes a ring system having at least one 5-, 6- or 7-membered heterocyclic ring, $R^4$ represents hydrogen, hydroxyl, alkyl, aryl, acyl or a heterocyclic group, including alkyl, aryl, acyl or heterocyclic groups which, together with at least one of the groups $R^1$ and $R^5$, complete a ring system having at least one 5-, 6- or 7-membered ring, or a nitrogen atom having two substituents, one of which is a hydrogen atom or an alkyl, aryl or acyl group, including alkyl, aryl or acyl groups which combine with $R^1$ to form a 5-, 6- or 7-membered heterocyclic ring containing at least one nitrogen atom, while the other substituent is a hydrogen atom or a group which combines with $R^5$ to form a 5-, 6- or 7-membered heterocyclic ring having at least one nitrogen atom, but the two substituents on the nitrogen atom must not both be hydrogen, $R^5$ represents hydrogen or a group which together with $R^1$ completes a 5-, 6- or 7-membered heterocyclic ring containing nitrogen, or which together with $R^4$ completes a 5-, 6- or 7-membered carbocyclic or heterocyclic ring, and X represents any colorless organic group.

ED compounds corresponding to the following formula (III) are particularly suitable:

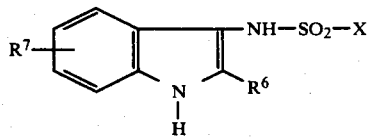

in which

X represents any colorless organic group, $R^6$ represents hydrogen, hydroxyl, alkyl, aryl, carbamoyl or sulfonylamino ($-NH-SO_2-R$, in which R represents alkyl, aryl or aralkyl), and $R^7$ represents hydrogen, alkyl, aryl, aralkyl, halogen, e.g. Cl, $NO_2$, CN, COOH, COOR, carbamoyl, $SO_3H$, sulfamoyl, acylamido, OH, OR, or acyloxy, in which R represents alkyl, aryl or aralkyl. $R^7$ may also represent two or more of the same or different substituents of the type defined above other than hydrogen, and two such substituents may complete a condensed benzene ring.

The alkyl groups defined above may be straight or branched chain alkyl groups having, for example 1 to 22 carbon atoms, e.g. methyl, ethyl, tert.-butyl, tert.-amyl, n-octyl, n-dodecyl, n-hexadecyl or n-octadecyl. The above mentioned aryl groups include in particular phenyl, which may in turn be substituted, e.g. with alkyl, alkoxy, alkylthio, alkylsulfonyl, hydroxyl, halogen or acylamino. For example, a phenyl group present as contain a hydroxyl group, preferably in the p- or o-position, or a substituent of the type mentioned above, preferably with a relatively long chain alkyl group. The aralkyl groups mentioned above include in particular the benzyl group. The carbamoyl or sulfamoyl groups mentioned may be unsubstituted or they may be substituted groups carrying one or two substituents in the form of alkyl, aryl or aralkyl groups in place of the hydrogen atoms on the nitrogen atom. The aforesaid acyl groups, which may be present, for example in the substituents $R^2$, $R^3$ and $R^4$ or in the acylamido and acyloxy groups which were mentioned as substituents in the definition of $R^6$ and $R^7$, may be derived from, for example, organic aliphatic or aromatic carboxylic or sulfonic acids or from carbamic acids, sulfamic acids or from semiesters of carbonic acid, such as acetyl, benzoyl, p-toluenesulfonyl, N-phenylcarbamoyl, N-n-octadecylsulfamoyl or phenoxycarbonyl.

Examples of rings completed by $R^1$ and $R^4$ include diazoline and diazinone rings and benzo condensed ring systems derived from them. The indole ring system is an example of a ring which may be completed by $R^1$ and $R^5$. Examples of rings completed by $R^4$ and $R^5$ include benzene rings, pyrazole rings and the naphthalene ring system.

The totality of the substituents in an ED compound according to the invention is preferably of such a nature that the ED compound is non-diffusing when incorporated in photographic layers. This may be achieved by, for example, ensuring that at least one of the substituents present, e.g. in ED compounds of the formula (II), at least one of the groups $R^1$, $R^4$ and $R^5$ or a group present either on a substituent in a ring completed by at least two of the aforesaid groups or on group X contains a group which confers diffusion resistance. Incorporation of the ED compounds in a diffusion resistant form is particularly desirable because the ED compounds are used in a particularly quantitative relationship to the corresponding non-diffusing reducible color providing compounds, and this relationship should, as far as possible, remain substantially unchanged even during prolonged storage of the photographic recording material.

Groups which may be regarded as conferring diffusion resistance are those which make it possible for the compounds according to the invention to be incorporated in a diffusion fast form in the hydrophilic colloids normally used in photographic materials. They are preferably organic groups, generally containing straight or branched chain aliphatic groups and optionally also containing carbocyclic or heterocyclic aromatic groups, generally with 8 to 20 carbon atoms. These groups which confer diffusion resistance are either directly attached to the remaining part of the molecule or attached indirectly, e.g. through one of the following groups: $-HNCO-$, $-NHSO_2-$, $-NR-$, in which R represents hydrogen or alkyl; $-O-$ or $-S-$. The group conferring diffusion resistance may also contain water-solubilizing groups, e.g. sulfo groups or carboxyl groups, and these may be present in an anionic form. Since the diffusion characteristics depend on the molecular size of the compound as a whole, relatively short chain groups, e.g. isoamyl or tert.-butyl groups, may be used in certain cases, e.g. if the molecule as a whole is large enough or if the ED compounds are emulsified in the layers by means of so-called oil formers or high boiling coupler solvents.

The following are examples of ED compounds according to the invention:

1.
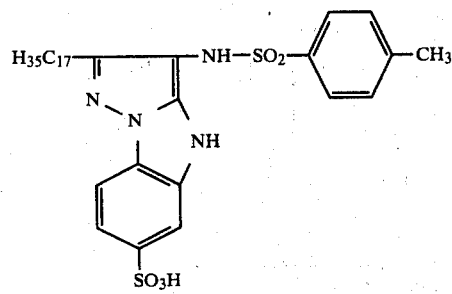
2.
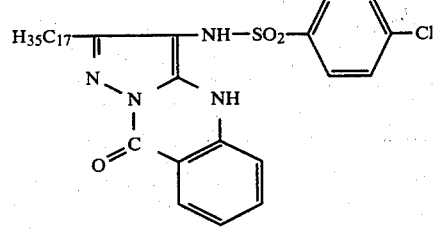
3.
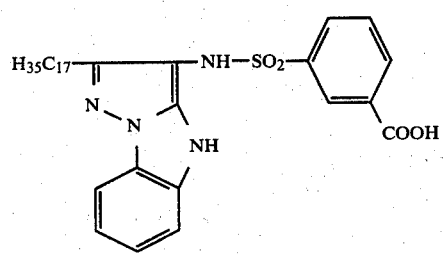
4.
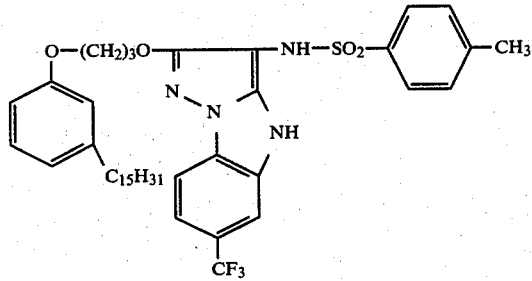
5.
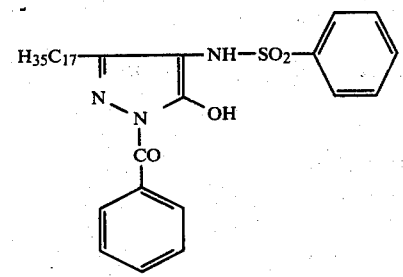
6.
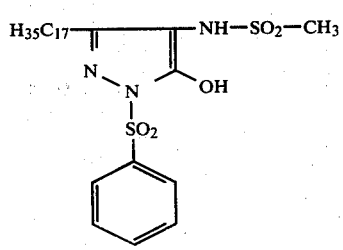
7.
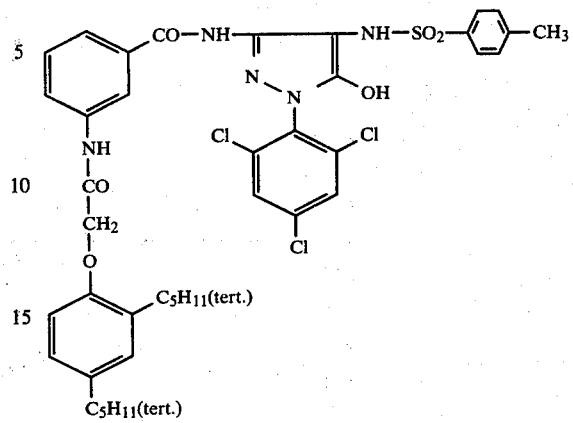
8.
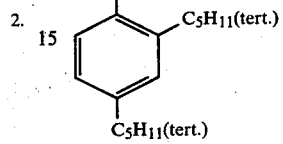
9.
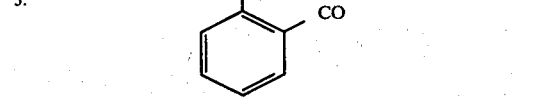
10.
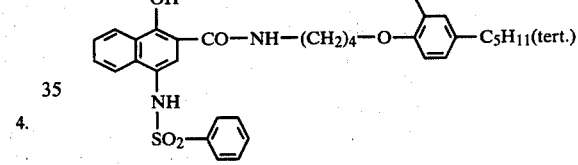
11.
12.
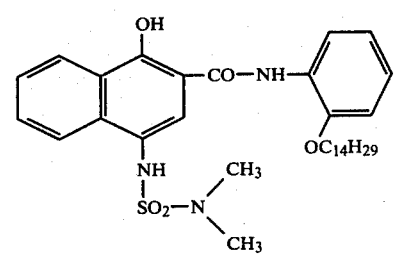

13. 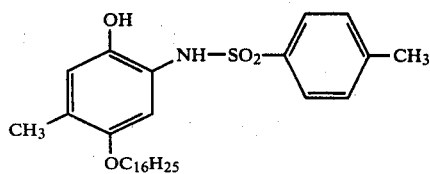

14. 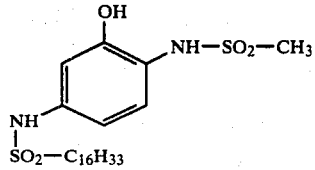

Compounds of formula (III)

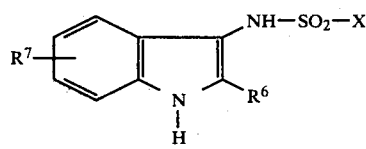

| Nr. | $R^6$ | $R^7$ | X |
|---|---|---|---|
| 15 | $-CONH-(CH_2)_4-O-$ phenyl-$C_5H_{11}(t)$, $C_5H_{11}(t)$ | 5-$OCH_3$ | phenyl-COOH |
| 16 | phenyl-$OC_{16}H_{33}$ | H | phenyl-$CH_3$ |
| 17 | phenyl | 5-NH-$SO_2$-phenyl-$CH_3$ | $-C_{16}H_{33}$ |
| 18 | phenyl | H | $-C_{16}H_{33}$ |
| 19 | phenyl | H | phenyl-$NHCONHC_{12}H_{25}$ |
| 20 | phenyl | H | phenyl-$NHCOC_{11}H_{23}$ |
| 21 | phenyl | 5-$NHCOC_{11}H_{23}$ | phenyl-$CH_3$ |
| 22 | phenyl | 5-$NHSO_2C_{16}H_{33}$ | phenyl-$CH_3$ |
| 23 | phenyl | 5-$NHSO_2C_{16}H_{33}$ | $-C_{16}H_{33}$ |
| 24 | phenyl | 5-$NHCOC_{11}H_{23}$ | $-CH_3$ |
| 25 | $-CH_3$ | 5-$NHCOC_{11}H_{23}$ | $-C_{16}H_{33}$ |
| 26 | phenyl-$OC_{16}H_{33}$ | H | phenyl-COOH |
| 27 | $-CON(CH_3)(C_{18}H_{37})$ | 5-$OCH_3$ | $-C_{16}H_{33}$ |

-continued

Compounds of formula (III)

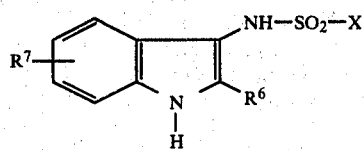

| Nr. | R⁶ | R⁷ | X |
|---|---|---|---|
| 28 | —CONH—C₁₈H₃₇ | 5-OCH₃ | 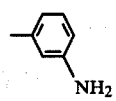 |

The ED compounds according to the invention are prepared by known methods, for example by first preparing compounds of the general formula (IV) in known manner:

$$R^1(-L^1=L^2)_n-NH_2 \quad (IV)$$

in which $R^1$, $L^1$, $L^2$ and n are as defined above, and then sulfonyl ating the resulting compounds of formula (IV) in known manner. Methods for the preparation of the intermediate compounds of formula (IV) have been described, for example, in German Offenlegungsschriften Nos. 2,242,762; 2,406,664; 2,505,248; 2,613,005 and 2,645,656.

The preparation of Compound No. 23 is described below by way of example.

COMPOUND NO. 23 step 1 5-Hexadecylsulfonylamino-2-phenyl-indole 20.8 g of 5-amino-2-phenylindole are dissolved in 200 ml of pyridine, and 32.45 g of hexadecylsulfonyl chloride are added. After stirring for 2 hours at room temperature, a precipitate is obtained by the addition of water. The precipitate is suction filtered and washed with water. It is then stirred into methanol in the cold, suction filtered and recrystallized from ethanol with the addition of a saturated aqueous sodium dithionite solution. The precipitate is suction filtered, washed with water and a little methanol and dried. 47.4 g of the above mentioned compound are obtained.

step 2
5-Hexadecylsulfonylamino-3-nitroso-2-phenylindole 42 g of the compound obtained as described under step 1 are suspended in 400 ml of glacial acetic acid. 11.76 g of sodium nitrite dissolved in 11 ml of water are added dropwise with stirring. The reaction mixture is then stirred for 2 hours and the precipitate is suction filtered, stirred into water, again suction filtered, stirred into methanol, suction filtered and dried. 42.5 g of the above mentioned compound are obtained.

step 3
3-Amino-5-hexadecylsulfonylamino-2-phenylindole 42.5 g of the compound obtained as described under step 2 are passed through a fine sieve and suspended in 400 ml of methanol. 34.8 g of sodium dithionite dissolved in 150 ml of water are added with stirring. The suspension is stirred for 4 hours at 50° C., its pH being adjusted to 9–10 by the addition of 2 N sodium hydroxide. When the reaction mixture is cold, the precipitate is suction filtered and washed with water and then with methanol. After drying, 38 g of the above mentioned compound, melting at 182° to 183° C., are obtained.

step 4 3,5-Bis-hexadecylsulfonylamino-3-phenylindole 6.6 g of hexadecylsulfochloride are added with stirring to 10.2 g of the compound obtained under step 3 in 100 ml of pyridine, and the mixture is stirred for 3 hours. A precipitate is obtained by the addition of water, suction filtered, washed with water and then stirred up with 100 ml of methylene chloride to form a suspension. The precipitate is suction filtered after the addition of methanol and dried. 14.4 g of the above mentioned compound (compound 23), melting point 210° to 212° C., are obtained.

The ED compounds according to the invention are superior to the known ED compounds, e.g. ascorbyl palmitate, in that they make it possible for higher maximum color densities and lower minimum color densities (fog) to be obtained.

Some of the ED compounds according to the invention have been described in Research Disclosure 17 842, February 1979. They are referred to therein as so-called "scavenger compounds" which compete with the color-providing compounds for the developer oxidation product. The color providing compounds mentioned in the said publication therefore differ from those used according to the invention in that they must be present in a form capable of being oxidized by developer oxidation products. The color providing compounds used according to the present invention are of a different type: they must be reduced before they release a diffusible dye. According to the invention, the ED compounds serve as reducing agents. It was not possible to conclude from the publication mentioned above that the compounds described would be capable of reducing the reducible color providing compounds used according to the invention, still less that they could do so with the desired stepwise graded reactivity. According to the invention, the ED compound reacts with the developer oxidation products provided before any significant reaction takes place with the color providing compound, with the result that the ED compound present is, to a large extent, used up in those areas where vigorous silver halide development takes place while in the other areas it releases diffusible dye by reaction with the color providing compound. When negative emulsions are used, therefore, the ED compound is used up in the exposed areas while diffusible dye is released in the unexposed areas and a positive diffusion image is obtained.

Suitable non-diffusing reducible color providing compounds for use in combination with the ED compounds according to the invention include, for example, the so-called BEND compounds of German Offenlegungsschrift No. 2,809,716 (BEND = "ballasted electron-accepting nucleophilic displacement"). In order to release the dye, these compounds require an intramolecular nucleophilic displacement reaction which is made possible by the reduction. Another type of suitable non-diffusing, reducible color providing compounds is the subject matter of the published European Patent Application No. 0,004,399.

For monochromatic processes, the color photographic recording material according to the invention contains at least one image producing layer unit, and for processes carried out to produce multicolored images, it generally contains at least three image producing layer units, each of which comprises at least one light-sensitive silver halide emulsion layer and, associated therewith, a combination of a non-diffusing reducible color providing compound and an electron donor compound, an ED compound according to the invention being used in at least one layer unit. As a general rule, one of the layer units is predominantly sensitive to blue light, another to green light and a third to red light; the associated color providing compounds in each case producing image dyes of the complementary color.

The terms "association" and "associated" are used in the sense that the arrangement of the silver halide emulsions, ED compound and color providing compound in relation to each other is such that they are capable of interacting to give rise to an imagewise correspondence between the silver image formed and the consumption of ED compound on the one and unused ED compound and color providing compound on the other hand so that an imagewise distribution of diffusible dye is produced to correspond to the undeveloped silver halide. The light-sensitive silver halide, color providing compound and ED compound need not necessarily be contained in the same layer in order to produce this result but may be accommodated in adjacent layers all belonging to the same layer unit. Separating layers are advantageously provided between the various layer units. These separating layers may contain compounds which react with diffusing development products to prevent their diffusion from one layer unit to another. This helps to restrict the "association" to one layer unit. Suitable compounds of this type are known and include, for example, non-diffusing hydroquinone derivatives as well as, for example, the so-called "scavenger compounds" described in the publication mentioned above, Research Disclosure No. 17 842. The ED compounds according to the invention may themselves take over this function if they are incorporated in a separating layer between two layer units.

The interaction between the exposed silver halide and the non-diffusing ED compound is generally brought about by the oxidized form of the silver halide developer used, which is oxidized by development, its oxidation product in turn being capable of oxidizing the ED compound and thereby removing it from the reaction with the color providing compound. The interaction between the unoxidized ED compound and the color providing compound is promoted by so-called electron transferring agents, which are preferably diffusible and capable of reversibly accepting and donating electrons. They are generally the same as the silver halide developers used.

Typical suitable electron transferring agents include, for example, hydroquinone compounds, e.g. hydroquinone, 2,5-dichlorohydroquinone and 2-chlorohydroquinone; aminophenol compounds such as 2-aminophenol, N-methylaminophenol, 3-methyl-4-aminophenol and 3,5-dibromoaminophenol; pyrocatechol compounds, e.g. pyrocatechol, 4-cyclohexyl-pyrocatechol, 3-methoxy-pyrocatechol and 4-(N-octadecylamino)-pyrocatechol; and phenyl diamine compounds e.g. N,N-diethyl-p-phenylenediamine, 3-methyl-N,N-diethyl-p-phenylenediamine, 3-methoxy-N-ethyl-N-hydroxyethyl-p-phenylenediamine and N,N,N',N'-tetramethyl-p-phenylenediamine.

According to a particularly advantageous embodiment of the invention, the electron transferring agent used in a 3-pyrazolidone compound, of which the following are specific examples: 1-Phenyl-3-pyrazolidone; 1-phenyl-4,4-dimethyl-3-pyrazolidone 4-hydroxymethyl-4-methyl-1-phenyl-3-pyrazolidone; 1-m-tolyl-3-pyrazolidone; 1-p-tolyl-3-pyrazolidone; 1-phenyl-4-methyl-3-pyrazolidone; 1-phenyl-5-methyl-3-pyrazolidone 1-phenyl-4,4-bis(hydroxymethyl)-3-pyrazlidone; 1,4-dimethyl-3-pyrazolidone; 4-methyl-3-pyrazolidone; 4,4-dimethyl-3-pyrazolidone; 1-(3-chlorophenyl)-4-methyl-3-pyrazolidone; 1-(4-chlorophenyl)-4-methyl-3-pyrazolidone; 1-(4-chlorophenyl)-3-pyrazolidone; 1-(4-tolyl)-4-methyl-3-pyrazolidone; 1-(2-tolyl)-4-methyl-3-pyrazolidone; 1-(4-tolyl)-4-hydroxymethyl-4-methyl-3-pyrazolidone; 1-(3-tolyl)-3-pyrazlidone; 1-(3-tolyl)-4,4-dimethyl-3-pyrazolidone; 1-(2-trifluoroethyl)-4,4-dimethyl-3-pyrazolidone and 5-methyl-3-pyrazolidone.

A combination of various electron transferring agents may be used, e.g. a combination such as that described in U.S. Pat. No. 3,039,869.

The developer compounds may be used in the development liquid or they may at least partially be introduced into any layer or layers of the photographic recording material, e.g. into one or more silver halide emulsion layers, layers containing the color providing compounds, intermediate layers, image receiving layers, and the like.

The optimum electron transferring compound for any particular case depends, of course, on the ED compound used as well as on the non-diffusing reducible, color providing compound and on the conditions under which development of the recording material is carried out.

The non-diffusing reducible color providing compound is generally used in sufficient quantity in a layer to produce a color image with a very high maximum color density, e.g. in a quantity of from 1 to $20 \cdot 10^{-4}$ mol/m$^2$. The quantity in which the ED compound according to the invention is used is adapted to that of the colour producing compound and should be sufficient to produce as high as possible a maximum color density, i.e. to effect as far as possible complete reduction of the color providing compound. At the same time, the quantity should not be substantially greater than is necessary for this purpose, in order that in the exposed areas it may, as far as possible, be completely used up by the development of the exposed silver halide. The most suitable quantitative proportions of silver halide to ED compound to color providing compound in any particular case may be determined by routine tests. Useful results may be obtained, for example if the quantity of ED compound is in the region of $0.2 \cdot 10^{-3}$ to $4 \cdot 10^{-3}$ mol/m$^2$, based on the quantity of color providing compound.

The light-sensitive element used for carrying out the dye diffusion transfer process generally contains one or more silver halide emulsion layer units and the non-diffusing color providing compounds and ED compounds associated with these units, and an image receiving element in which the desired color image is produced by imagewise transfer of the diffusible dyes. To achieve this transfer, firm contact must be established between the light-sensitive element and the image receiving element for at least a finite period of time during development so that the imagewise distribution of diffusible dyes obtained in the light-sensitive element as a result of development can be transferred to the image receiving element. This content may be established after development has started or it may have already been established before the onset of development. Such contact before development occurs, for example, in cases where the dye diffusion transfer process is carried out using a so-called integral recording material in which the light-sensitive element and the image receiving element form an integral unit, also referred to hereinafter as monosheet material, which is preserved even after completion of the development process, i.e. the light-sensitive element is not separated from the image receiving element even after completion transfer of the dyes. Such an embodiment has been described, for example, in German Offenlegungsschrift No. 2,019,430.

The image receiving element may thus form part of the color photographic recording material, e.g. in the form of an image receiving layer situated on a transparent support below the light-sensitive silver halide emulsion layer units. In that case, a light impermeable, preferably light reflecting layer of binder is suitably arranged between the image receiving layer and the light-sensitive layers. The image receiving layer, which, in another embodiment of the dye diffusion transfer process, may also be arranged on a separate support (image receiving sheet), generally contains, in known manner, a basic mordant for diffusible anionic (acid) dyes.

The mordants used for acid dyes are preferably long chain quaternary ammonium or phosphonium compounds or tertiary sulfonium compounds, e.g. those described in U.S. Pat. Nos. 3,271,147 and 3,271,148. Certain metal salts and their hydroxides which form difficultly soluble compounds with the acid dyes may also be used. The dye mordants are dispersed in one of the usual hydrophilic binders in the receptor layer, e.g. in gelatine, polyvinyl pyrrolidone or partially or completely hydrolysed cellulose esters. Some binders may, of course, themselves function as mordants, e.g. copolymers or polymer mixtures of vinyl alcohol and N-vinylpyrrolidone, as described, for example, in German Auslegeschrift No. 1,130,284, or polymers of quaternary bases containing nitrogen, e.g. polymers of N-methyl-2-vinylpyridine, as described, for example, in U.S. Pat. No. 2,484,430. Other binders which are suitable as mordants include, for example, guanyl hydrazone derivatives of alkyl vinyl ketone polymers as described in U.S. Pat. No. 2,882,156 or guanyl hydrazone derivatives of acylstyrene polymers as described, for example, in German Offenlegungsschrift No. 2,009,498 but when the last mentioned mordanting binders are used, other binders, e.g. gelatine would generally also be added. Other polymeric mordants have been described, e.g. in U.S. Pat. No. 3,709,690 and German Offenlegungsschriften Nos. 2,315,304; 2,445,782; 2,551,786 and 2,631,521.

The color photographic recording material according to the invention may also contain acid layers and so-called retarding or timing layers which together form a so-called neutralisation system. Such a system may be arranged in known manner between the support layer and the image receiving layer on it, or it may be arranged in some other position in the layer unit, e.g. more above the light-sensitive layers, i.e. remote from these layers, when viewed from the image receiving layer. The neutralisation system is generally orientated so that the retarding layer is situated between the acid layer and the position where the alkaline development liquid or paste acts. Such acid layers, retarding layers or neutralisation systems comprising both have been disclosed, for example, in U.S. Pat. Nos. 2,584,030, 2,983,606; 3,362,819 and 3,362,821 and German Offenlegungsschriften Nos. 2,455,762; 2,601,653; 2,716,505; 2,601,653; 2,716,505 and 2,816,878. Such a neutralisation system may, in known manner also contain two or more retarding layers.

In a particular embodiment, the recording material according to the invention may also contain one or more pigmented opaque layers which are permeable to aqueous liquids. These layers may fulfil two functions. Firstly, they may prevent unwanted access of light to the light-sensitive layers and secondly, such a pigment layer may form an aesthetically pleasing background to the dye image produced, especially if the layer contains a light colored or white pigment such as $TiO_2$. Integral color photographic recording materials containing such a pigment layer are known, e.g. from U.S. Pat. No. 2,513,181 and German Auslegeschrift No. 1,924,430. Instead of providing a preformed opaque layer, means for producing such a layer during the development process may be provided. Such pigment layers may be composed of two or more partial layers according to the two functions mentioned above. One of these partial layers may contain, for example, a white pigment and the other, for example a dark, light absorbent pigment such as carbon black.

According to a particularly preferred embodiment of the invention, the photographic material is an integral color photographic recording material monosheets for carrying out the dye diffusion transfer process and comprises, for example, the following layer elements:

(1) a transparent support layer
(2) an image receiving layer
(3) a light impermeable layer
(4) a light-sensitive element having at least one light-sensitive silver halide emulsion layer and, associated therewith, at least one non-diffusing, color providing compound and an ED compound
(5) a retarding layer
(6) an acid polymer layer
(7) a transparent support layer.

The monosheet material may be arranged in two parts prepared separately from one another, namely the light-sensitive part (layer elements 1 to 4) and the cover sheet (layer elements 5 to 7). These two parts are then placed together with their active sides in contact and joined together, optionally using spacer strips so that a space is left between the two parts for an accurately measured quantity of development liquid. The layer elements 5 and 6, which together form the neutralisation system, may also be arranged between the support layer and the image receiving layer of the light-sensitive part, but in that case their sequence is reversed.

Means for introducing a development liquid between the light-sensitive part and the cover sheet may be provided, e.g. in the form of a rupturable container which is arranged at the side and discharges its contents between two adjacent layers of the monosheet material when subjected to a mechanical force.

The developer preparation may contain developer compounds in addition to the aqueous alkali, but these must then be adjusted to the nature of the color providing compounds. Other possible components of the developer preparation include thickeners for increasing the viscosity, e.g. hydroxyethyl cellulose; silver halide solvents, e.g. sodium thiosulfate or one of the bis-sulfonyl-alkane compounds described in German Offenlegungsschrift No. 2,126,661, and clouding agents to produce opaque layers, e.g. pigments of TiO$_2$, ZnO, barium stearate or kaolin. Some of these constituents may alternatively or in addition be incorporated in one or more layers of the color photographic recording material according to the invention.

EXAMPLE

Preparation of the dispersions

1. Cyan dye:

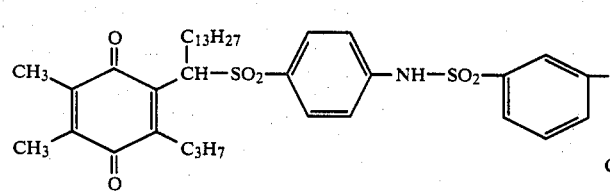

81.5 ml of distilled water
5 g of gelatine
5 g of cyan dye
3 ml of wetting agent Lomar D, 40% (naphthalene sulfonate condensate, trade product of Nopco, USA)
5 ml of isopropanol
0.5 g of sodium acetate
The mixture is milled in a sand mill.

2. Magenta dye:

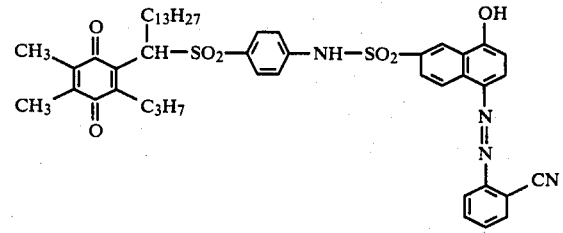

93 ml of distilled water
1.9 g of gelatine
1.9 g of magenta dye
1.14 ml of wetting agent Lomar D, 40%
1.9 ml of isopropanol
0.5 g of sodium acetate
The mixture is milled in a sand mill.

3. 4-Methyl-1-phenyl-3-pyrazolidone

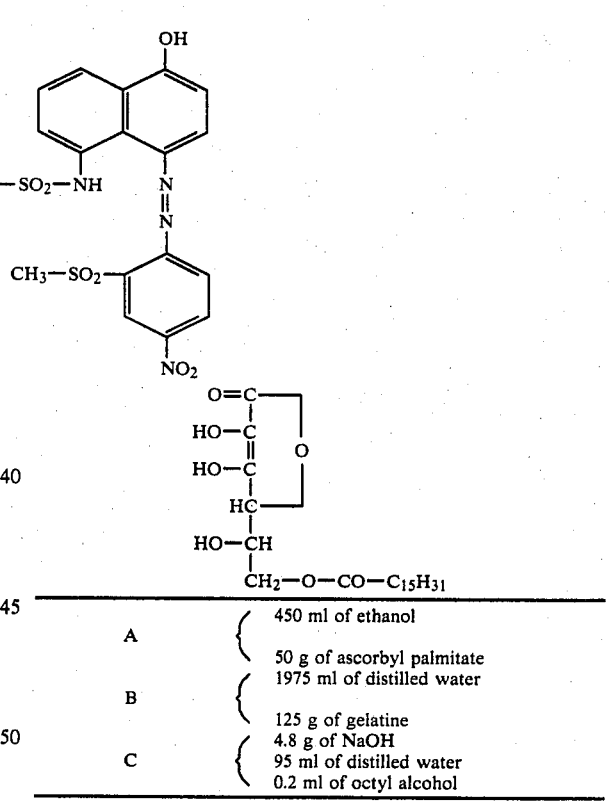

850 ml of distilled water
40 g of gelatine
100 g of 4-methyl-1-phenyl-3-pyrazolidone
10 ml of wetting agent Lomar D 40%
The mixture is milled in a sand mill.

4. Ascorbyl palmitate (ED compound for comparison)

| | |
|---|---|
| A | 450 ml of ethanol |
| | 50 g of ascorbyl palmitate |
| B | 1975 ml of distilled water |
| | 125 g of gelatine |
| C | 4.8 g of NaOH |
| | 95 ml of distilled water |
| | 0.2 ml of octyl alcohol |

Solution A is introduced into a mixture of solutions B and C with rapid stirring.

5. ED compound 16 (according to the invention)

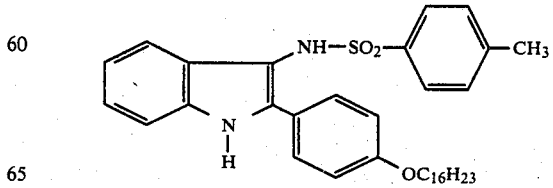

68 ml of distilled water
4 g of gelatine 4 g of ED compound 16
4 ml of N-methylpyrrolidone
ED compound 16 is dissolved in ethyl acetate and N-methylpyrrolidone; the dissolved gelatine is then added and the ethyl acetate is evaporated off.

Dispersions are prepared by the same method from ED compounds 9, 14, 17, 19, 21, 23 and 24 according to the invention.

Preparation of the light-sensitive materials

A silver halide emulsion layer containing dye and ED compound was applied to an opaque support layer of polyethylene laminated paper, as described below for materials I to XII. A protective layer with phenidone having the composition indicated below was then poured over the silver halide emulsion layer:
938.5 ml of distilled water
27.5 g of gelatine
24 g of dispersion of 4-methyl-1-phenyl-3-pyrazolidone
10 ml of wetting agent FT-248 (trade product of Bayer, Leverkusen).

Several light-sensitive materials were prepared by this method, using the following casting solutions for the silver halide emulsion layers:

Material I
145 g of silver chloride emulsion containing 86 g of $AgNO_3$ per kg and having a gelatine/silver ratio of 1.2,
155 ml of distilled water,
54 g of cyan dye dispersion,
270 g of ascorbyl palmitate dispersion
366 ml of distilled water and
10 ml of wetting agent Hostapon-T, 5% (trade product of Hoechst).

The silver halide emulsion, dye dispersion and dispersion of the ED compound were melted separately at 40° C. First the dye and then the ED compound and wetting agent were added to the melted emulsion.
Wet application: 100 g/m²

| Dry application per m²: | |
|---|---|
| Silver halide: | 1207 mg = 7 mMol |
| Cyan dye: | 253 mg = 0.232 mMol |
| Ascorbyl palmitate: | 497.5 mg = 1.2 mMol |
| Gelatine: | 2939 mg |

Material II
145 g of silver chloride emulsion,
155 ml of distilled water,
54 g of dispersion of the cyan dye,
117 g of dispersion of ED compound 16
119 ml of distilled water
10 ml of wetting agennt Hostapon-T, 5%
Preparation of mixture as for Material I
Wet application: 60 g/m²

| Dry application per m²: | |
|---|---|
| Silver halide: | 1207 mg = 7 mMol |
| Cyan dye: | 253 mg = 0.232 mMol |
| ED compound 16 | 726 mg = 1.2 mMol |
| Gelatine: | 2422 mg |

Material III
145 g of silver chloride emulsion
155 ml of distilled water
115 g of dispersion of the magenta dye
270 g of dispersion of ascorbyl palmitate
105 ml of distilled water
10 ml of wetting agent Hostapon-T
Preparation of mixture as for Material I
Wet application: 80 g/m²

| Dry application per m²: | |
|---|---|
| Silver halide: | 1207 mg = 7 mMol |
| Magenta dye: | 216.6 mg = 0.230 mMol |
| Ascorbyl palmitate: | 497.5 mg = 1.2 mMol |
| Gelatine: | 2902 mg |

Material IV
145 g of silver chloride emulsion,
155 ml of distilled water,
115 g of dispersion of the magenta dye,
117 g of dispersion of ED compound 16,
285 ml of distilled water
10 ml of wetting agent Hostapon-T
Preparation of mixture as for Material I
Wet application: 80 g/m²

| Dry application per m²: | |
|---|---|
| Silver halide: | 1207 mg = 7 mMol |
| Magenta dye: | 216.6 mg = 0.230 mMol |
| ED compound 16: | 726 mg = 1.2 mMol |
| Gelatin: | 2385 mg |

Material V–XI were prepared by the same method as Material II, using ED compounds Nos. 9, 14, 17, 19, 21, 23 and 24 in place of ED compound 16 according to the invention, in the same molar quantities.

Material XII was prepared by the same method as material IV, using ED compound 19 according to the invention instead of ED compound 16 according to the invention.

Preparation of the image receiving sheet

An image receiving layer (mordanting layer) having the following composition was applied to an opaque support layer of polyethylene laminated paper:
658 ml of distilled water
72 g of gelatine
10 ml of wetting agent FC-126 (trade product of 3 M)
100 ml of ethanol
22 g of hexadecyl-triphenyl-phosphonium bromide,
128 ml of distilled water,
10 ml of 4% formaldehyde.
Wet application: 65 g/m²

| Dry application per m²: | |
|---|---|
| Gelatine: | 4680 mg |
| Mordant: | 1430 mg. |

A protective layer obtained from the following casting solution was applied to the image receiving layer:
943 ml of distilled water
40 g of gelatine
10 ml of wetting agent FT-248
7 ml of 4% formaldehyde.
Wet application: 40 g/m²

| Dry application: | |
|---|---|
| (gelatine) | 160 mg/m². |

Light-sensitive materials I–XII were exposed for 60 seconds to a 75 Watt incandescent lamp behind a step wedge and developed for one minute in a commercial CP 38 apparatus in contact with an image receiving sheet as described above, using a developer having the following composition:

7 g of sodium hydroxide
25 g of $Na_3PO_4$
80 ml of N-methylpyrrolidone
20 ml of 1-phenyl-5-mercaptotetrazole (1% methanolic solution)
5 g of KBr
made up to 1000 ml with water.

The colour wedges obtained were examined with a RD 514 Macbeth densitometer. The maximum and minimum color densities obtained are entered in the following Table.

TABLE

| Material | ED Compound | Cyan $D_{min}$ | Cyan $D_{max}$ | Magenta $D_{min}$ | Magenta $D_{max}$ |
|---|---|---|---|---|---|
| I | AP | 0.01 | 0.53 | | |
| II | 16 | 0.17 | 1.99 | | |
| III | AP | | | 0.03 | 0.14 |
| IV | 16 | | | 0.10 | 0.80 |
| V | 9 | 0.02 | 0.77 | | |
| VI | 14 | 0.02 | 0.74 | | |
| VII | 17 | 0.26 | 1.82 | | |
| VIII | 19 | 0.14 | 1.85 | | |
| IX | 21 | 0.15 | 1.48 | | |
| X | 23 | 0.49 | 1.98 | | |
| XI | 24 | 0.36 | 1.88 | | |
| XII | 19 | | | 0.10 | 1.23 |

AP = ascorbyl palmitate

We claim:

1. In a color photographic recording material comprising at least one light-sensitive silver halide emulsion layer unit and, associated with this unit, a combination of a non-diffusing, reducible color providing compound which, in the reduced state, is capable of releasing a diffusible dye under alkaline development conditions, and an electron donor compound (ED compound) which is capable of reducing the non-diffusing, reducible color providing compound under the alkaline development conditions, the improvement according to which the material contains, as ED compound, a compound corresponding to the following general formula:

$$R^1(-L^1=L^2)_n-NH-SO_2-X$$

in which $L^1$, $L^2$ each represent a methine group

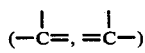

which may be a member of an at least partially unsaturated carbocyclic or heterocyclic ring system, $R^1$ represents $-OR^2$, $-SR^2$ or $-NHR^3$,
$R^2$ represents hydrogen or a group which is capable of being hydrolysed under the conditions of photographic development,
$R^3$ represents hydrogen, alkyl, aryl, acyl or a group which together with the nitrogen atom defined in $R^1$ and with $L^1$, optionally with the inclusion of $L^2$, completes a ring system having at least one 5-, 6- or 7-membered heterocyclic ring,
n represents 1 or 2, and
X represents any colorless organic group,
at least $R^1$, $L^1$, $L^2$ or a ring completed by the said groups ($R^1$, $L^1$, $L^2$) or X contains a group which confers diffusion resistance.

2. The color photographic recording material as claimed in claim 1 which contains as ED compound, a compound corresponding to the following general formula:

$$R^1-C(R^4)=C(R^5)-NH-SO_2-X$$

in which $R^1$ represents $-OR^2$, $-SR^2$ or $-NHR^3$,
$R^2$ represents hydrogen or a group capable of being hydrolysed under the conditions of photographic development,
$R^3$ represents hydrogen, alkyl, aryl, acyl or a group which, together with $R^4$ or $R^5$ or with $R^4$ and $R^5$ completes a ring system having at least one 5- 6- or 7-membered heterocyclic ring,
$R^4$ represents hydrogen, hydroxyl, alkyl, aryl or acyl, including those alkyl, aryl and acyl groups which together with at least one of the groups $R^1$ and $R^5$ complete a ring system having at least one 5-, 6- or 7-membered ring, or it represents a nitrogen atom having two substituents, one of which substituents is a hydrogen atom or an alkyl aryl or acyl group, including those alkyl, aryl and acyl groups which together with $R^1$ complete a 5-, 6- or 7-membered heterocyclic ring having at least one nitrogen atom, the other substituent being a hydrogen atom or a group which together with $R^5$ completes a 5-, 6- or 7-membered heterocyclic ring having at least one nitrogen atom, but the two substituents on the nitrogen atom must not both be hydrogen,
$R^5$ represents hydrogen or a group which together with $R^1$ completes a 5-, 6- or 7-membered heterocyclic ring containing nitrogen or together with $R^4$ completes a 5-, 6- or 7-membered carbocyclic or heterocyclic ring, and
X represents any colorless organic group, at least one of the groups $R^1$, $R^4$, $R^5$ or a substituent on a ring completed by at least two of the aforesaid groups, or the group X containing a group which confers diffusion resistance.

3. In a color photographic recording material comprising at least one light-sensitive silver halide emulsion layer unit and, associated with this unit, a combination of a non-diffusing, reducible color providing compound which, in the reduced state, is capable of releasing a diffusible dye under alkaline development conditions, and an electron donor compound (ED compound) which is capable of reducing the non-diffusing, reducible color providing compound under the alkaline development conditions, the improvement according to which the material contains, as ED compound, a compound corresponding to the following general formula:

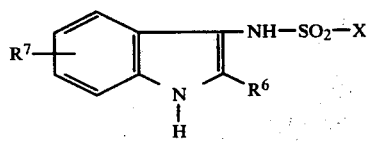

in which

X represents any colorless organic group,
$R^6$ represents hydrogen, hydroxyl, alkyl, aryl, carbamoyl or sulfonylamino ($-NH-SO_2R$, in which R represents alkyl, aryl or aralkyl), and
$R^7$ represents hydrogen or alkyl, aryl, aralkyl, halogen, $NO_2$, CN, COOH, COOR, carbamoyl, $SO_3H$, sulfamoyl, acylamido, OH, OR or acyloxy, in which R represents alkyl, aryl or aralkyl, at least one of the groups $R^6$, $R^7$ and X containing a group which confers diffusion resistance.

* * * * *